United States Patent
Odidi et al.

(10) Patent No.: US 10,624,858 B2
(45) Date of Patent: Apr. 21, 2020

(54) CONTROLLED RELEASE COMPOSITION USING TRANSITION COATING, AND METHOD OF PREPARING SAME

(75) Inventors: Isa Odidi, Toronto (CA); Amina Odidi, Toronto (CA)

(73) Assignee: INTELLIPHARMACEUTICS CORP, Toronto (CA)

( * ) Notice: Subject to any disclaimer, the term of this patent is extended or adjusted under 35 U.S.C. 154(b) by 0 days.

(21) Appl. No.: 10/924,649

(22) Filed: Aug. 23, 2004

(65) Prior Publication Data
US 2006/0039976 A1 Feb. 23, 2006

(51) Int. Cl.
*A61K 9/28* (2006.01)
(52) U.S. Cl.
CPC .................. *A61K 9/2886* (2013.01)
(58) Field of Classification Search
CPC ........................................... A61K 9/2886
See application file for complete search history.

(56) References Cited

U.S. PATENT DOCUMENTS

| | | |
|---|---|---|
| 2,540,979 A | 2/1951 | MacDonnell |
| 3,254,088 A | 5/1966 | Juda et al. |
| 3,493,657 A | 2/1970 | Lewenstein |
| 3,629,393 A | 12/1971 | Nakamoto et al. |
| 3,728,445 A | 4/1973 | Bardani |
| 3,773,955 A | 11/1973 | Pachter |
| 3,789,117 A | 1/1974 | Tsujino |
| 3,819,706 A | 6/1974 | Menta |
| 3,845,770 A | 11/1974 | Higuchi |
| 3,856,721 A | 12/1974 | Fritschel |
| 3,916,899 A | 11/1975 | Theeuwes et al. |
| 4,008,719 A | 2/1977 | Theeuwes |
| 4,016,880 A | 4/1977 | Theeuwes |
| 4,034,758 A | 7/1977 | Theeuwes |
| 4,036,228 A | 7/1977 | Theeuwes |
| 4,045,563 A | 8/1977 | Berntsson et al. |
| 4,060,598 A | 11/1977 | Groppenbacher et al. |
| 4,077,407 A | 3/1978 | Theeuwes |
| 4,160,452 A | 7/1979 | Theeuwes |
| 4,161,477 A | 7/1979 | Long |

(Continued)

FOREIGN PATENT DOCUMENTS

| | | |
|---|---|---|
| CA | 2286684 A1 | 10/1998 |
| CA | 2529984 A1 | 12/2004 |

(Continued)

OTHER PUBLICATIONS

Dashevsky, A. pH-independent release of basic drug from pellets coated with the extended release polymer dispersion Kollicoat SR 30 D and the enteric polymer dispersion Kollicoat MAE 30 DP. European Journal of Pharmaceutics and Biopharmaceutics. 58 (2004) 45-49. Available online Jun. 1, 2004.*

(Continued)

*Primary Examiner* — Rachael E Bredefeld
(74) *Attorney, Agent, or Firm* — Thomas | Horstemeyer, LLP

(57) ABSTRACT

The present invention is concerned with the use of transition coating and transition coating composition to control and or target the release of active pharmaceutical ingredients, and biological, chemical, neutraceutical, agricultural and nutritional materials and a method of preparing controlled release systems utilizing these components.

10 Claims, 2 Drawing Sheets

(56) References Cited

U.S. PATENT DOCUMENTS

| | | |
|---|---|---|
| 4,183,838 A | 1/1980 | Gagliani |
| 4,183,839 A | 1/1980 | Gagliani |
| 4,193,985 A | 3/1980 | Bechgaard |
| 4,200,098 A | 4/1980 | Ayer |
| 4,218,433 A | 8/1980 | Kooichi et al. |
| 4,248,856 A | 2/1981 | Guley et al. |
| 4,250,136 A | 2/1981 | Rex |
| 4,252,786 A | 2/1981 | Weiss et al. |
| 4,255,431 A | 3/1981 | Junggren et al. |
| 4,309,405 A | 1/1982 | Guley et al. |
| 4,327,725 A | 5/1982 | Cortese |
| 4,330,338 A | 5/1982 | Banker |
| 4,337,257 A | 6/1982 | Junggren |
| 4,389,393 A | 6/1983 | Schor et al. |
| 4,425,441 A | 1/1984 | Gagliani et al. |
| 4,457,933 A | 7/1984 | Gordon |
| 4,461,759 A | 7/1984 | Dunn |
| 4,486,412 A | 12/1984 | Shah et al. |
| 4,508,905 A | 4/1985 | Junggren |
| 4,514,538 A | 4/1985 | Shvakhman et al. |
| 4,517,112 A | 5/1985 | Mardis et al. |
| 4,518,717 A | 5/1985 | Long et al. |
| 4,545,412 A | 10/1985 | Gamberini |
| 4,582,835 A | 4/1986 | Lewis |
| 4,606,909 A | 8/1986 | Bechgaard |
| 4,610,870 A | 9/1986 | Jain et al. |
| 4,612,008 A | 9/1986 | Wong et al. |
| 4,628,098 A | 12/1986 | Nohara et al. |
| 4,666,705 A | 5/1987 | DeCrosta et al. |
| 4,676,929 A | 6/1987 | Rittler |
| 4,684,516 A | 8/1987 | Bhutani |
| 4,686,230 A | 8/1987 | Rainer et al. |
| 4,689,333 A | 8/1987 | Nohara et al. |
| 4,704,285 A | 11/1987 | Alderman |
| 4,708,834 A | 11/1987 | Cohen et al. |
| 4,713,248 A | 12/1987 | Kjornaes et al. |
| 4,728,512 A | 3/1988 | Mehta |
| 4,756,911 A | 7/1988 | Drost et al. |
| 4,758,579 A | 7/1988 | Kohl et al. |
| 4,765,989 A | 8/1988 | Wong et al. |
| 4,783,337 A | 11/1988 | Wong et al. |
| 4,786,505 A | 11/1988 | Lovgren et al. |
| 4,812,446 A | 3/1989 | Brand |
| 4,818,760 A | 4/1989 | Binder et al. |
| 4,832,958 A | 5/1989 | Baudier et al. |
| 4,844,905 A | 7/1989 | Ichikawa et al. |
| 4,844,909 A | 7/1989 | Goldie |
| 4,845,118 A | 7/1989 | Lang et al. |
| 4,851,228 A | 7/1989 | Zentner et al. |
| 4,853,230 A | 8/1989 | Lovgren et al. |
| 4,869,908 A | 9/1989 | Kirschner et al. |
| 4,880,631 A | 11/1989 | Haslam |
| 4,886,668 A | 12/1989 | Haslam |
| 4,891,223 A | 1/1990 | Ambegaonkar et al. |
| 4,892,742 A | 1/1990 | Shah |
| 4,900,557 A | 2/1990 | Dell et al. |
| 4,904,476 A | 2/1990 | Mehta et al. |
| 4,927,640 A | 5/1990 | Dahlinder et al. |
| 4,935,243 A | 6/1990 | Borkan et al. |
| 4,940,587 A | 7/1990 | Jenkins et al. |
| 4,940,588 A | 7/1990 | Sparks et al. |
| 4,946,853 A | 8/1990 | Bannon et al. |
| 4,963,365 A | 10/1990 | Samejima et al. |
| 4,965,269 A | 10/1990 | Brandstrom et al. |
| 4,966,768 A | 10/1990 | Michelucci et al. |
| 5,000,962 A | 3/1991 | Sangekar et al. |
| 5,004,614 A | 4/1991 | Staniforth |
| 5,021,433 A | 6/1991 | Alminger et al. |
| 5,028,434 A | 7/1991 | Barclay et al. |
| 5,045,552 A | 9/1991 | Souda et al. |
| 5,049,394 A | 9/1991 | Howard et al. |
| 5,071,643 A | 12/1991 | Yu et al. |
| 5,073,384 A | 12/1991 | Valentine et al. |
| 5,077,051 A | 12/1991 | Gallopo |
| 5,123,146 A | 6/1992 | Olson |
| 5,149,702 A | 9/1992 | Yamada et al. |
| 5,190,763 A | 3/1993 | Edgren et al. |
| 5,202,128 A | 4/1993 | Morella et al. |
| 5,219,572 A | 6/1993 | Sivaramakrishnan |
| 5,229,131 A | 7/1993 | Amidon et al. |
| 5,236,714 A | 8/1993 | Lee et al. |
| 5,240,712 A | 8/1993 | Smith |
| 5,252,339 A | 10/1993 | Cristofori et al. |
| 5,260,069 A | 11/1993 | Chen |
| 5,286,497 A | 2/1994 | Hendrickson et al. |
| 5,288,500 A | 2/1994 | Ibsen |
| 5,290,816 A | 3/1994 | Blumberg |
| 5,300,291 A | 4/1994 | Sablotsky |
| 5,330,766 A | 7/1994 | Morella et al. |
| 5,376,388 A | 12/1994 | Meyers |
| 5,378,474 A | 1/1995 | Morella et al. |
| 5,393,528 A | 2/1995 | Staab |
| 5,415,871 A | 5/1995 | Pankhania et al. |
| 5,425,950 A | 6/1995 | Dandiker et al. |
| 5,430,042 A | 7/1995 | Lindberg et al. |
| 5,445,829 A | 8/1995 | Paradissis et al. |
| 5,458,887 A | 10/1995 | Chen et al. |
| 5,472,711 A | 12/1995 | Baichwal |
| 5,480,335 A | 1/1996 | Caveza |
| 5,503,846 A | 4/1996 | Wehling |
| 5,508,040 A | 4/1996 | Chen |
| 5,527,545 A | 6/1996 | Santus et al. |
| 5,595,762 A | 1/1997 | Derrieu |
| 5,681,581 A | 10/1997 | Dunn |
| 5,681,585 A * | 10/1997 | Oshlack ............... A61K 9/1617 424/461 |
| 5,708,017 A | 1/1998 | Dave et al. |
| 5,713,000 A | 1/1998 | Larson |
| 5,736,159 A | 4/1998 | Chen et al. |
| 5,753,265 A | 5/1998 | Bergstrand |
| 5,759,577 A | 6/1998 | Barcomb |
| 5,760,121 A | 6/1998 | Beall et al. |
| 5,780,055 A | 7/1998 | Habib et al. |
| 5,783,215 A | 7/1998 | Arwidsson et al. |
| 5,795,583 A | 8/1998 | Grune et al. |
| 5,800,422 A | 9/1998 | Dong et al. |
| 5,817,338 A | 10/1998 | Bergstrand |
| 5,840,329 A | 11/1998 | Bai |
| 5,840,910 A | 11/1998 | Souda et al. |
| 5,879,708 A | 3/1999 | Makino et al. |
| 5,955,106 A | 9/1999 | Moeckel et al. |
| 5,972,329 A | 10/1999 | Chuang et al. |
| 5,998,445 A | 12/1999 | Souda et al. |
| 6,022,562 A | 2/2000 | Autant et al. |
| 6,039,975 A | 3/2000 | Shah et al. |
| 6,046,177 A | 4/2000 | Stella et al. |
| 6,068,853 A | 5/2000 | Giannos et al. |
| 6,068,856 A * | 5/2000 | Sachs .................. A61K 9/2886 424/474 |
| 6,090,401 A | 7/2000 | Gowan et al. |
| 6,099,859 A | 8/2000 | Cheng et al. |
| 6,106,864 A | 8/2000 | Dolan et al. |
| 6,183,776 B1 | 2/2001 | Depui et al. |
| 6,183,777 B1 | 2/2001 | Chen et al. |
| 6,194,001 B1 | 2/2001 | Gribbon et al. |
| 6,210,710 B1 | 4/2001 | Skinner |
| 6,228,400 B1 | 5/2001 | Lee et al. |
| 6,251,432 B1 | 6/2001 | Mazer et al. |
| 6,261,582 B1 | 7/2001 | Needham et al. |
| 6,270,804 B1 | 8/2001 | Getz et al. |
| 6,296,876 B1 | 10/2001 | Odidi et al. |
| 6,312,723 B1 | 11/2001 | Whittle et al. |
| 6,312,724 B1 | 11/2001 | Odidi et al. |
| 6,368,635 B1 | 4/2002 | Akiyama et al. |
| 6,433,040 B1 | 8/2002 | Dellamary et al. |
| 6,479,075 B1 | 11/2002 | Odidi et al. |
| 6,489,346 B1 | 12/2002 | Phillips |
| 6,491,949 B2 | 12/2002 | Faour et al. |
| 6,509,037 B2 | 1/2003 | Odidi |
| 6,527,051 B1 | 3/2003 | Reddy et al. |
| 6,555,127 B2 | 4/2003 | Steiner |
| 6,558,704 B1 | 5/2003 | Bartholomaeus et al. |
| 6,569,453 B2 | 5/2003 | Linder et al. |
| 6,599,529 B1 | 7/2003 | Skinhoj |

(56) References Cited

U.S. PATENT DOCUMENTS

| | | | |
|---|---|---|---|
| 6,605,300 B1 | 8/2003 | Burnside et al. | |
| 6,607,751 B1 | 8/2003 | Odidi et al. | |
| 6,627,635 B2 | 9/2003 | Palermo et al. | |
| 6,645,524 B2 | 11/2003 | Midha et al. | |
| 6,645,528 B1 | 11/2003 | Straub et al. | |
| 6,645,988 B2 | 11/2003 | Phillips | |
| 6,652,882 B1 | 11/2003 | Odidi et al. | |
| 6,673,367 B1 | 1/2004 | Goldenheim et al. | |
| 6,676,966 B1 * | 1/2004 | Odidi et al. | 424/464 |
| 6,696,088 B2 | 2/2004 | Oshlack et al. | |
| 6,699,885 B2 | 3/2004 | Phillips | |
| 6,780,882 B2 | 8/2004 | Phillips | |
| 6,800,668 B1 | 10/2004 | Odidi et al. | |
| 6,902,742 B2 | 6/2005 | Devane et al. | |
| 6,911,217 B1 | 6/2005 | Gren et al. | |
| 6,946,146 B2 | 9/2005 | Mulye | |
| 6,991,804 B2 | 1/2006 | Helmus et al. | |
| 7,090,867 B2 | 8/2006 | Odidi et al. | |
| 7,135,465 B2 | 11/2006 | Abramowitz et al. | |
| 7,157,103 B2 | 1/2007 | Sackler | |
| 7,858,119 B1 | 12/2010 | Odidi et al. | |
| 7,906,143 B1 | 3/2011 | Odidi et al. | |
| 9,078,827 B2 | 7/2015 | Odidi | |
| 2001/0006649 A1 | 7/2001 | Chen | |
| 2002/0002147 A1 | 1/2002 | Abramowitz et al. | |
| 2002/0045646 A1 | 4/2002 | Phillips | |
| 2002/0064099 A1 | 5/2002 | Wyssbrod et al. | |
| 2002/0086885 A1 | 7/2002 | Odaka et al. | |
| 2002/0110590 A1 | 8/2002 | Shaked et al. | |
| 2002/0128293 A1 | 9/2002 | Rampal et al. | |
| 2002/0132005 A1 | 9/2002 | Faour | |
| 2002/0150535 A1 | 10/2002 | Madras et al. | |
| 2003/0064099 A1 | 4/2003 | Oshlack et al. | |
| 2003/0064101 A1 | 4/2003 | Mehta et al. | |
| 2003/0068370 A1 | 4/2003 | Sackler | |
| 2003/0068371 A1 | 4/2003 | Oshlack et al. | |
| 2003/0077297 A1 | 4/2003 | Chen et al. | |
| 2003/0118641 A1 | 6/2003 | Maloney et al. | |
| 2003/0118669 A1 | 6/2003 | Phillips | |
| 2003/0185887 A1 | 10/2003 | Chen et al. | |
| 2003/0215507 A1 | 11/2003 | Sherman et al. | |
| 2003/0215527 A1 | 11/2003 | Phillips | |
| 2003/0220413 A1 * | 11/2003 | Petereit et al. | 523/105 |
| 2003/0235616 A1 | 12/2003 | Sowden et al. | |
| 2004/0048896 A1 | 3/2004 | Phillips | |
| 2004/0058018 A1 | 3/2004 | Phillips | |
| 2004/0101558 A1 | 5/2004 | Dietrich et al. | |
| 2004/0131669 A1 | 7/2004 | Kerc | |
| 2004/0171646 A1 | 9/2004 | Phillips | |
| 2004/0185093 A1 | 9/2004 | Szymczak | |
| 2004/0198775 A1 | 10/2004 | Fraser et al. | |
| 2004/0265370 A1 | 12/2004 | Odidi et al. | |
| 2004/0265380 A1 | 12/2004 | Delmas et al. | |
| 2005/0004171 A1 | 1/2005 | Phillips | |
| 2005/0042304 A1 | 2/2005 | Phillips | |
| 2005/0054682 A1 | 3/2005 | Phillips | |
| 2005/0129778 A1 * | 6/2005 | Mulye | A61K 9/1676 424/490 |
| 2005/0186268 A1 | 8/2005 | Hoshi et al. | |
| 2005/0191349 A1 * | 9/2005 | Boehm et al. | 424/464 |
| 2005/0196436 A1 | 9/2005 | Chantranukul et al. | |
| 2005/0214373 A1 * | 9/2005 | Desai et al. | 424/472 |
| 2006/0003001 A1 | 1/2006 | Devane et al. | |
| 2006/0003007 A1 | 1/2006 | Odidi et al. | |
| 2006/0004193 A1 | 1/2006 | Muller | |
| 2006/0018948 A1 | 1/2006 | Guire et al. | |
| 2006/0024361 A1 | 2/2006 | Odidi et al. | |
| 2006/0039864 A1 | 2/2006 | Bartholomaus et al. | |
| 2006/0039976 A1 | 2/2006 | Odidi et al. | |
| 2006/0099246 A1 | 5/2006 | Tanner et al. | |
| 2006/0017336 A1 | 6/2006 | Knauff | |
| 2006/0153909 A1 | 7/2006 | Motoune | |
| 2006/0205681 A1 | 9/2006 | Moaddeb | |
| 2007/0003619 A1 | 1/2007 | Smith | |
| 2007/0009589 A1 | 1/2007 | Raghupathi et al. | |
| 2007/0077293 A1 | 4/2007 | Park | |
| 2007/0104778 A1 | 5/2007 | Zeng et al. | |
| 2007/0131357 A1 | 6/2007 | Wu | |
| 2007/0166370 A1 | 7/2007 | Odidi et al. | |
| 2007/0286902 A1 | 12/2007 | Xie et al. | |
| 2009/0220613 A1 | 9/2009 | Odidi et al. | |

FOREIGN PATENT DOCUMENTS

| | | | |
|---|---|---|---|
| CA | 2551946 | 7/2005 | |
| CN | 1634116 A | 7/2005 | |
| DE | 1204363 | 8/1964 | |
| DE | 3531487 C2 | 8/1985 | |
| DE | 39 43 242 | 6/1990 | ............... A61K 9/16 |
| DE | 3943242 A1 | 6/1990 | |
| DE | 19635676 A1 | 3/1998 | |
| EP | 0005129 B1 | 4/1981 | |
| EP | 0157695 A2 | 9/1985 | |
| EP | 0166287 B1 | 1/1986 | |
| EP | 0174726 A1 | 3/1986 | |
| EP | 0184322 B1 | 6/1986 | |
| EP | 0234485 B1 | 9/1987 | |
| EP | 080341 B1 | 10/1987 | |
| EP | 0261478 A1 | 3/1988 | |
| EP | 0268956 B1 | 6/1988 | |
| EP | 0270305 A2 | 6/1988 | |
| EP | 0342522 A1 | 11/1989 | |
| EP | 0366321 A1 | 5/1990 | |
| EP | 0403383 A1 | 12/1990 | |
| EP | 0434999 B1 | 7/1991 | |
| EP | 0453001 A1 | 10/1991 | |
| EP | 0 516 141 | 5/1992 | ............... A61K 9/50 |
| EP | 0527638 A1 | 2/1993 | |
| EP | 0533790 B1 | 3/1993 | |
| EP | 0797991 A1 | 10/1997 | |
| EP | 0960620 A1 | 12/1999 | |
| EP | 1017370 B1 | 7/2000 | |
| EP | 1493435 | 1/2005 | |
| EP | 1731142 A1 | 12/2006 | |
| FR | 2419722 A1 | 1/1979 | |
| FR | 2624012 | 9/1989 | |
| FR | 2778848 | 11/1999 | |
| GB | 2134516 A | 8/1984 | |
| GB | 2163747 A | 3/1986 | |
| HU | 203477 B | 1/1991 | |
| JP | 2002-068964 | 3/2002 | |
| JP | 2005500364 | 1/2005 | |
| JP | 2005508359 | 3/2005 | |
| JP | 2005515153 | 5/2005 | |
| WO | WO8503436 A1 | 8/1985 | |
| WO | WO8705212 A1 | 9/1987 | |
| WO | WO9011070 A1 | 10/1990 | |
| WO | WO9107950 A1 | 6/1991 | |
| WO | WO9116885 A1 | 11/1991 | |
| WO | WO9119710 A1 | 12/1991 | |
| WO | WO9204013 A1 | 3/1992 | |
| WO | WO9208716 A1 | 5/1992 | |
| WO | WO9323770 A1 | 7/1993 | |
| WO | WO9428882 A1 | 12/1994 | |
| WO | WO9816206 * | 4/1998 | ............... A61K 9/48 |
| WO | WO9816206 A1 | 4/1998 | |
| WO | WO9851287 A1 | 11/1998 | |
| WO | WO9912524 A1 | 3/1999 | |
| WO | 02/30398 A2 | 4/2002 | |
| WO | 0230398 | 4/2002 | |
| WO | 0230398 A2 | 4/2002 | |
| WO | WO0230398 A2 | 4/2002 | |
| WO | 03013538 A1 | 2/2003 | |
| WO | 2003013476 A1 | 2/2003 | |
| WO | W003009846 A1 | 2/2003 | |
| WO | 03086364 A1 | 10/2003 | |
| WO | WO04000825 A1 | 12/2003 | |
| WO | 200402418 A2 | 3/2004 | |
| WO | 2004024128 | 3/2004 | |
| WO | 2004050023 A2 | 6/2004 | |
| WO | 2004056354 A1 | 7/2004 | |
| WO | WO04056354 A1 | 7/2004 | |
| WO | 2005021009 A2 | 3/2005 | |
| WO | WO0137817 A1 | 3/2005 | |

(56) References Cited

FOREIGN PATENT DOCUMENTS

| WO | 2005032474 | | 4/2005 |
|---|---|---|---|
| WO | 2005065661 | A2 | 7/2005 |
| WO | 2005097075 | | 10/2005 |
| WO | 2005097075 | A2 | 10/2005 |
| WO | 2005099674 | A1 | 10/2005 |
| WO | 2006011592 | | 2/2006 |
| WO | 2006017336 | A2 | 2/2006 |
| WO | 2006085335 | A2 | 8/2006 |
| WO | 2007082770 | A1 | 7/2007 |
| WO | 2008122993 | A1 | 10/2008 |
| WO | 2009113061 | A1 | 9/2009 |
| WO | 2010044842 | A1 | 4/2010 |
| WO | 2012002644 | A2 | 1/2012 |

OTHER PUBLICATIONS

Venkatraman et. al. Chapter 22, An Overview of Controlled Release Systems, Handbook of Pharmaceutical Controlled Release Technology by Donald Wise. Published 2002. p. 443.*
Porro et al, Digest Liver Dis 2000; 32: 201-208.*
Anderson, M. et al., Analysis of Film Coating Thickness and Surface Area of Pharmaceutical Pellets using Fluorescence Microscopy and Image Analysis, J. Pharmaceutical and Biomedical Analysis, (2000), vol. 22, pp. 325-339.
Arora, S. et al. Pulsatie Drug Delivery Systems: An Approach for Controlled Drug Delivery, Indian J. Pharm. Sci., (2006). vol. 68, pp. 295-300.
Aulton, M.E., Pharmaceutics: The Science of Dosage Form Design, (1988), pp. 316-321, (Churchill Livingstone Ed.).
Banga. A. et al., "Incorporation of Simethicone into Syrup or Clear Base Liquid Orals", Drug Development and Industrial Pharmacy, (1989), vol. 15(5), pp. 671-704.
Conner, A. L. et al., A Scintigraphic Study to Investigate the Potential for Altered Gut Distribution of Loperaminde from a Loperaminde-Simethicone Formation in Man, European Journal of Pharmaceutical Sciences, (2001), vol. 13, pp. 369-374.
Dashevsky, A. etal., pH-independent Release of Baisc Drug from Pellets Coated with the Extended Release Polymer Dispersion Kollicoat® SR 30 D and the Enteric Polymer Dispersion Kollicoat® MAE 30 DP. European Journal of Pharmaceutics and Biopharmaceuticals, (2004), vol. 58, pp. 45-49 (available online Jun. 1. 2004).
Deshpande, A. et al., Development of a Novel Controlled-Release System for Gastric Retention, Pharmaceutical Research, (1997), vol. 14, No. 6, pp. 815-819.
Krögel, I. et al., Floating of Pulsatile Drug Delivery Systems Based on Coated Efferescent Cores, International Journal of Pharmaceutics, (1999) vol. 187, pp. 175-184 anl.
Laizure, S. C. et al., Stability of Bupropion and its Major Metabolites in Human Plasma, Therapeutic Drug Monitoring (1985), vol. 7 (4); p. 447.
Lehmann, K. et al.,—Fast Disintegrating Controlled Release Tablets from Coated Panicles—Drugs Made in Germany. (1994) vol. 37. No. 2. pp. 53-60.
Martindale, The Extra Pharmacopoeia, 30th Ed. (The Pharmaceutical Press, London 1993).
Rakur, G. et al., 2-((2-Pyridylm-ethyl) Sulfiny) Benzimidazoles: Acid Sensitive Suicide Inhibitors of the Proton Transport System in the Parietal Cell, Biochem Biophys. Res. Comm. (1985), vol. 128, No. 1, pp. 477-484.
Remington's Pharmaceutical Sciences, 18th ed, (1990), Chapter 83, pp. 1539-1540.
Sathe, P.M. et al, Drug Product Performance, In Vitro, Generic Drug Product Development, (2004), vol. 143, Chapter 8, pp. 187-209.
Steward, P.A. Review of Pharmaceutical Controlled Release Method and Devices, (1995) 12 pages.
Sungthongjeen, S. et al.,—Development of Pulsatile Release Tablets with Swelling and Rupturable Layers, Journal of Controlled Release, (2004), vol. 95, pp. 1147-1159.

Sunshine, et al., "Analgesic Efficacy of Pentazocine Versus a Pentazocine-Naxloxone Combination Following Oral Administration", Clin. J. Pain, (1988), vol. 4, pp. 35-40.
Walters, S. M., Influence of pH on Hydrolytic Decomposition of Dimethylpropion Hydrochloride: Stability Studies on Drug Substance and Tables using High-Performance Liquid Chromatograph, J. Pharma Science, (1980), vol. 69 (10), p. 1208.
Wang, R. et al., Crossover and Parallel Study of Oral Analgesics, J. Clin. Pharmacl., (1981) Vo. 21, pp. 162-168.
Merriam-Webster Online Dictionary, http://www.meriam-webster.com/dictionary/prevent, obtained online Feb. 18, 2008.
Merriam-Webster Online Dictionary, http://www.meriam-webster.com/dictionary/cure, obtained online Dec. 16, 2009.
European Patent Application No. 04 737 76.2-2112, Examination Report dated Nov. 18, 2009.
Office Action for U.S. Appl. No. 10/561,700 dated Dec. 27, 2007.
Office Action for U.S. Appl. No. 10/561,700 dated Mar. 18, 2008.
Office Action for U.S. Appl. No. 10/561,700 dated Apr. 17, 2009.
Office Action for U.S. Appl. No. 10/561,700 dated Sep. 3, 2009.
Office Action for U.S. Appl. No. 10/861,809 dated Sep. 28, 2009.
Office Action for U.S. Appl. No. 10/861,809 dated Nov. 26, 2008.
Office Action for U.S. Appl. No. 10/861,809 dated Nov. 13, 2007.
Office Action for U.S. Appl. No. 12/092,654 dated Mar. 12, 2010.
Office Action for Canadian Patent Application No. 2,626,558 dated Nov. 25, 2009.
English translation of Office Action dated Oct. 13, 2010 corresponding to Chinese Patent Application No. 200780019372.7.
International Search Report and Written Opinion; PCT/CA2007/000540.
International Search Report and Written Opinion; PCT/CA2007/000548.
International Search Report and Written Opinion; PCTCA2007/000550.
International Search Report and Written Opinion; PCT/CA2007/000862.
International Search Report and Written Opinion dated Aug. 31, 2007; PCT/CA2007/000862.
International Preliminary Report on Patentability dated Nov. 27, 2008; PCT/CA2007/000862.
International Preliminary Examination Report; PCT/CA2002/01360.
International Search Report; PCT/CA2002/01360.
International Search Report; PCT/CA2002/00054.
International Search Report and Written Opinion; PCT/CA2004/000825.
Encyclopaedia of Polymer Science and Technology; vol. 10 (1969); published by John Wiley & Sons.
U.S. Appl. No. 11/473,386.
U.S. Appl. No. 09/947,464.
U.S. Appl. No. 10/561,700.
U.S. Appl. No. 12/696,118.
U.S. Appl. No. 12/225,956.
U.S. Appl. No. 12/225,954.
U.S. Appl. No. 11/432,226.
U.S. Appl. No. 12/092,654.
U.S. Appl. No. 10/924,649.
U.S. Appl. No. 10/900,415.
U.S. Appl. No. 10/880,474.
U.S. Appl. No. 11/315,868.
Canadian Intellectual Property Office, Office Action dated Nov. 15, 2013 in CA application 2,579,382, 2 pages.
Canadian Intellectual Property Office, Office Action dated Dec. 4, 2013 in CA application 2,648,278, 3 pages.
European Patent Office, Examination Report dated Sep. 24, 2013 for EP application 07 719 478.5-1455, 6 pages.
Super Disintegrants: Characterization and Function (From European Examination Report of #3 above), 2007 by Informa Healthcare USA, Inc., 18 pages.
Ganesh Rasve, et al.; Pulsatile Drug Delivery System: Current Scenario; International Journal of Pharma and Bio Sciences; vol. 2 / Issue 3/ Jul.-Sep. 2011; 12 pages.
International Search Report from PCT/CA2013/000610; dated Sep. 18, 2013; Prepared by Nasreddine Slougui on Sep. 13, 2013.

(56) References Cited

OTHER PUBLICATIONS

Torpac, Capsul Size Chart, 2000, pp. 1-3.
Supplemental European Search Report Prepared by Miralles J. Gimenez dated Aug. 23, 2012.
Supplemental European Search Report Prepared by Antonio Raposo dated Aug. 2, 2012.
Paste, www.thefreedictionary.com/paste, accessed Jun. 26, 2012.
Paste, http://www.thefreedictionary.com/paste,accessed Jun. 29, 2012.
Merriam-Webster Dictionary; definition of "Paste"; 1 page, accessed Dec. 16, 2014.
Office Action dated Dec. 7, 2016; Canadian Intellectual Property Office; application 2,648,278; 4 pages.
Office Action for European Patent Application No. 07719784.6 dated Jul. 6, 2018.
Canadian Examination Search Report, 50 rue Victoria, Place du Portage 1, Gatineau Quebec K1A 0C9; dated Sep. 29, 2017. 4 pages, Application No. 2,648,278.
Buhse, Lucinda, et al. "Topical drug classification." international journal of pharmaceutics 295 (2005): 101-112.
Zulfiker et al., "Formulation Development Using Maize Starch & Avicel PH101 as Disintegrating Agents and Their Effect on Physical Characteristics & In Vitro Release Profile." International Journal of Pharmaceutical Sciences and Research 2011, vol. 2(8), pp. 2136-2141.

\* cited by examiner

Figure 2. Suggested mechanism of drug release from transition coated systems.
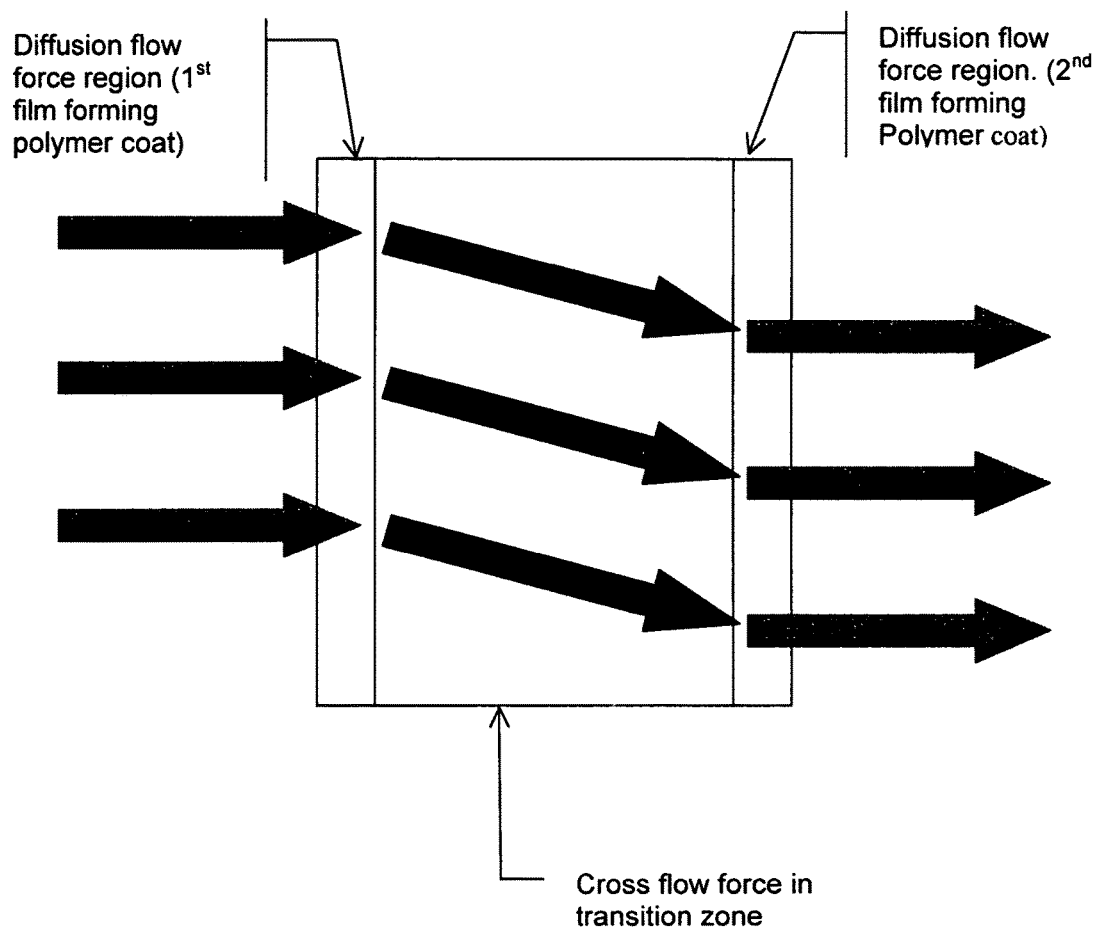

CONTROLLED RELEASE COMPOSITION USING TRANSITION COATING, AND METHOD OF PREPARING SAME

FIELD OF THE INVENTION

The present invention relates to a novel composition and to a method of using and preparing same in order to control the rate and extent of delivery of granules, tablets, capsules, spheroids, pellets, microspheres, nanospheres, microcapsules, crystals or particles containing one or more of the following; active pharmaceutical ingredients; biological, chemical, nutraceutical, agricultural or nutritional materials. This is accomplished by the use of coats of two or more polymers in which the various layers of coat of each polymer are either contiguous or non contiguous and transition from one coat to another.

BACKGROUND OF THE INVENTION

The prior art teaches the use of sustained-release systems, with the aim of providing medicaments which can be administered once a day. Orally administered solid dosage forms have gained more grounds in this respect.

DE Patent Application No. 39 43 242 (FR No. 2 670 112) discloses "matrix" type granules comprising active pharmaceutical ingredients (API) and inert excipient(s) compressible into tablets. Each granule consists of a multitude of said particles included in a roughly spherical matrix comprising a cellulosic polymer, a vinylic or acrylic polymer, a plasticizer and a lubricating agent.

There are reports in the literature of several tablets which are film-coated with a coating material of, for example, cellulosic, acrylic, starch, polyethylene glycol or gum type, or their derivatives. This coating functions to provide taste masking, protection of API, gastro-resistance to physiological fluids, and also to prolong the release of active pharmaceutical ingredients.

For example, U.S. Pat. No. 4,461,759 describes a coated tablet which protects the API from the harmful effects of the acid pH of the stomach and at the same time releasing the API at a constant rate in the gastrointestinal tract.

The use of microporous film coating which allows the release of the API under the effect of an osmotic pressure has also been widely reported. One such report teaches the sustained release of API irrespective of the solubility of the API in the medium. This embodiment is described in patent application WO 91/16885 and in U.S. Pat. No. 5,028,434.

Another practice in the delivery of drugs that abounds in the prior art is the use of micro-particulate pharmaceutical systems giving a sustained release of API.

For example, Patent EP 396,425 discloses a system intended for the administration once daily dose of API. To this end, the API is bound to the surface of inert spherules with a diameter ranging from 250 to 2000 microns, using a known binder. The particles are then film-coated with a cellulose compound and a plasticizer, to slow down the release of the API.

U.S. Pat. No. 5,286,497 describes a formulation based on Diltiazem (AP) which is designed to be taken once a day. The API is bound to the surface of inert granules of sugar or of starch, which are then optionally film-coated.

U.S. Pat. No. 4,869,908 describes floating tablets, characterized by a long residence time in the stomach. This system is more particularly suited to the administration of API having a preferential absorption at the gastric level.

Patent FR 2,395,026 teaches a process for the preparation of a system in which the micro-particles containing the API are in a sustained-release form containing, in their composition, a densifying agent which allows a significant prolongation in the transit time, which may then exceed 24 hours. This system was developed after observation of the fact that transit in the small intestine is slowed down considerably when the density of the particles exceeds 1.4 grams per cubic centimeter. The same approach of increasing the transit time by elevation of the density is adopted in EP applications 0,080,341 and 0,173,210. However, such systems have the drawback of requiring the introduction of a large amount of densifying agent, of the order of 30 to 80% of the total weight of the form, which limits the content of API in the system and constitutes a handicap for the manufacture of forms requiring a large dose of API.

Another approach for controlled release consists of the development of bioadhesive systems.

EP 0,452,268 claims a bucco-adhesive system in the form of microparticles film-coated with a gel of xanthan/carob gums or with ethylcellulose. The effectiveness of such a system, essentially intended for the mouth, is not established, and all the less so since the particles are coated with a film of wax as an outer layer, which is intended to sustain their release but which makes adhesion improbable, and anyway not demonstrated in vivo.

Application EP 0,516,141 is directed towards the development of a bioadhesive particulate system by overcoating, of any given sustained-release form of an AP, with an adhesive composition based on polymers such as water-soluble derivatives of cellulose, acrylic polymers known under the trade names Carbopol® or Polycarbophil®, alginates, gelatin or pectin.

The above described prior art are clearly distinct from the features disclosed in the current invention, more especially by their composition and manufacturing process.

A review of the prior art reveals a large number of unsuccessful attempts directed towards providing a general solution to the controlled release of API for periods which may be up to 24 hours in the case of oral administrations.

Furthermore, none of the prior art takes account of the set of constraints inherent in the production of a multifunctional system which may be applied to the majority of APIs, and no satisfactory solution is available to date.

Indeed, there are a large number of constraints opposing the production of such a system, and there are many difficulties to be solved.

U.S. Pat. No. 6,022,562 discloses an invention which relates to microcapsules for the oral administration of medicinal and/or nutritional API, which are smaller than or equal to 1000 microns in size. These microcapsules consist of particles which are coated with a coating material consisting of a mixture of a film-forming polymer derivative, a hydrophobic plasticizer, a functional agent and a nitrogen-containing polymer. The invention also relates to a process for the production of the said microcapsules.

The claims in U.S. Pat. No. 6,022,562 and the other patents cited from the prior art are significantly different from our disclosure. U.S. Pat. No. 6,022,562 uses multiple film forming polymers in one film forming coating composition, i.e., the polymers are applied as an admixture to form one or more layers of coat. Unlike in our invention there is no attempt to separate each film forming polymer from the other. To the best of our knowledge, there is no prior art teaching the use of multiple polymers each applied separately as a coat, neither does the prior art teach the use of transition coats to modulate the release of materials.

There have been reports in the literature of the use of hydrophobic thermoplastic polymers such as ethylcellulose for the controlled release of pharmaceutical substances. Ethylcellulose is typically applied as a coat. Drug release is by symmetric flow (channel flow) and diffusion through the ethylcellulose layer. Release is controlled by the layer thickness and the rate of channel flow or diffusion flow force. Such systems are at a disadvantage because they allow drug delivery to be controlled via a singular property i.e., coating thickness formed from use of a single film forming admixture. This presents a high risk approach to the optimization of formulations, because the use of coating thickness as an index for controlling rate of input presents a narrow window to work with and limits the applicability of such systems. This is one reason why matrix systems have superceded the use of hydrophobic thermoplastic polymers such as ethylcellulose coats or coats consisting of a mixture of ethylcellulose polymer and a nitrogen-containing polymer such as polyvinylpyrolidone as means for controlling the release of drugs. As stated earlier to the best of our knowledge there is no report in the prior art where more than one thermoplastic polymer has been used to control the release of drugs in which the polymers are applied as transition coats. The object of the present invention is thus to provide a novel composition and a method of using and preparing same in order to control the rate and extent of delivery of granules, tablets, capsules, spheroids, pellets, microspheres, nanospheres, microcapsules, crystals or particles containing one or more of the following; active pharmaceutical ingredients, biological, chemical, nutraceutical, agricultural or nutritional materials. This consists of the use of coats of two or more polymers in which the respective layers of coat of each polymer transition from one coat to another and are not applied as an admixture.

SUMMARY OF THE INVENTION

We have unexpectedly discovered in our laboratory that combining two or more polymer coats in a transition type assembly in which the layers of coat for a select group of polymers are deposited in a manner such that there is transition from one coat to another provides a much wider scope for formulation optimization. Moreover, it has been surprisingly found that the control of rate of input or drug release is much easier, cost effective and efficient with these systems. Release control may be effected or optimized through the types of polymers used, the order in which they are deposited, the number and or width of transition zones or boundaries, the ratios of the polymers in the mix and the nature of their interaction at the transition zones. The mechanism of release in the transition type coating as taught in this invention is far superior and significantly different from the non-transition type coating taught in the prior art. By transition coating, cross flow of drug molecules is introduced at the transition boundary. When placed in contact with liquid milieu, systems on which transition coats have been applied will experience diffusion flow followed by cross flow. The net effect is asymmetric flow which results in a liquid funnel or funnel flow as drug molecules or materials migrate from the core past a transition zone. It is our opinion that, due to the low tortuosity factor of the pre-transition zone, the flow is laminar leading to a diffusion flow force field. Adjacent to this is the transition zone having a higher tortuosity factor in which a second force field is generated by the turbulent or funnel flow. This force field is the cross flow force field. The funnel flow that results helps create a velocity gradient.

The invention is thus comprised of granules, tablets, capsules, spheroids, pellets, microspheres, nanospheres, microcapsules, crystals or particles containing one or more of the following; active pharmaceutical ingredients; biological, chemical, nutraceutical, agricultural or nutritional materials to which has been applied layers of coat of two or more polymers such that there is a transition from one coat to another with a transition zone or boundary formed at the zone of first contact of the respective coats.

The present invention is further directed to a method of treating a disease for which the active pharmaceutical ingredient in the dosage form is effective, comprising administering to a mammal in need of such treatment the timed, pulsed, chronotherapeutic, controlled or extended release pharmaceutical composition of the present invention. Another aspect of the present invention is directed to the method of making the timed, pulsed, chronotherapeutic, controlled or extended release pharmaceutical composition of the present invention.

BRIEF DESCRIPTION OF THE DRAWINGS

FIG. 2 illustrates an embodiment of a mechanism of drug release from transition coated systems.

DETAILED DESCRIPTION OF THE INVENTION

Figure 1:
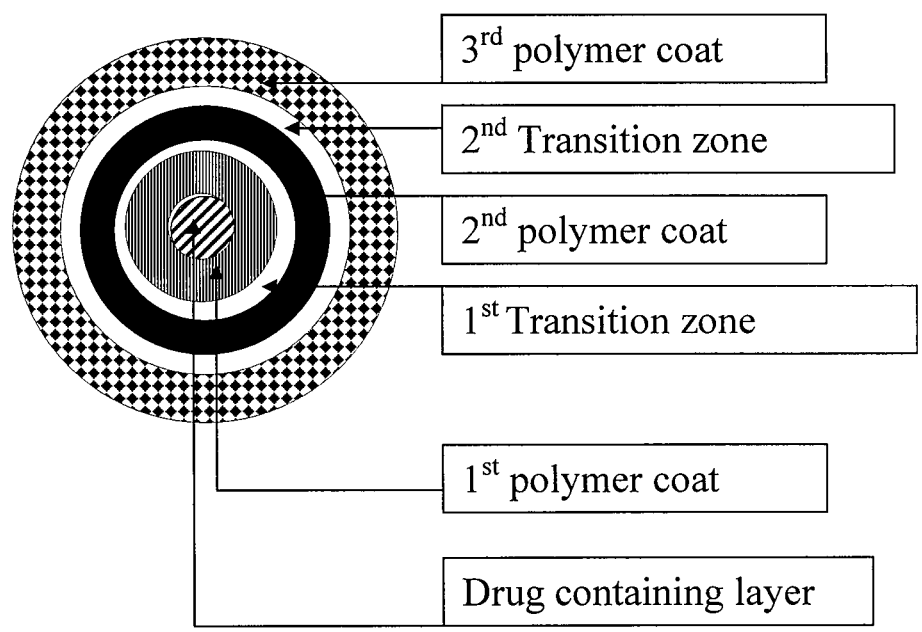
FIG. 1 illustrates an example of a transition coated microparticle showing three polymer coats and two transition zones.

In the present invention the granules, tablets, capsules, spheroids, pellets, microspheres, nanospheres, microcapsules, crystals or particles containing one or more of the following; active pharmaceutical ingredients; biological, chemical, nutraceutical, agricultural or nutritional materials can be prepared by wet or dry granulation, by extrusion spheronization, by powder or solution layering, by microencapsulation techniques, by milling and compression techniques. The transition coating may be carried out using fluid bed coating techniques or by coating using perforated side vented pan coating technique or by microincapsultion technique. These methods have been previously taught in the prior art. One approach which we teach, is a multiple wet granulation and drying technique. This involves the granulation of the active ingredient with or without excipients with the first film forming polymer solution or dispersion and drying the granulation in an oven or fluid bed or vacuum drying. The wet granules may be milled or screened before drying. The coated dried granules may be milled. The process is repeated using the dried or dried milled granules as starting material and the second film forming polymer solution or dispersion as granulation liquid. This process is repeated as many times as necessary to obtain the required number of transition coats. The capsules used in this invention may be hard or soft gelatin type or made from cellulose ethers.

As used herein, the term "active pharmaceutical ingredients" refers to chemical or biological molecules providing a therapeutic, diagnostic, or prophylactic effect in vivo.

Active pharmaceutical ingredients contemplated for use in the compositions described herein include the following categories and examples of drugs and alternative forms of these drugs such as their metabolites or pro-drugs, alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthamatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, venlafaxine, paroxetine, and protriptyline); antidiabetics (e.g., sulfonylurea derivatives); antifungal agents (e.g., griseofulvin, amphotericin B, nystatin, and candicidin); antihypertensive agents (e.g., propanolol, propafenone, oxyprenolol, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan); antianxiety agents (e.g., lorazepam, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, divalproex, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nisoldipine; and nitrates such as nitroglycerin, isosorbide dinitrate, pentaerythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, respiridone, and prochlorperazine); antimanic agents (e.g., lithium carbonate); antiarrhythmics (e.g., bretylium tosylate, esmolol, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillamine, salsalate, piroxicam, azathioprine, indomethacin, meclofenamate, gold sodium thiomalate, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibriolytic agents (e.g., aminocaproic acid); hemorheologic agents (e.g., pentoxifylline): antiplatelet agents (e.g., aspirin); anticonvulsants (e.g., valproic acid, divalproex sodium, phenytoin, phenytoin sodium, clonazepam, primidone, phenobarbitol, amobarbital sodium, methsuximide, metharbital, mephobarbital, mephenytoin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, loratadine, and); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate, steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, tolbutamide, and tolazamide); hypolipidemic agents (e.g., clofibrate, dextrothyroxine sodium, probucol, simvastatin, pravastatin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); oil-soluble vitamins (e.g., vitamins A, D, E, K, and the like); as well as other drugs such as mitotane, halonitrosoureas, anthrocyclines, and ellipticine.

A description of these and other classes of useful drugs and a listing of species within each class can be found in Martindale, The Extra Pharmacopoeia, 30th Ed. (The Pharmaceutical Press, London 1993), and Physician Desk Reference (PDR®) (published by Medical Economics Company, Inc. Montvale, N.J.) the disclosure of which is incorporated herein by reference in its entirety.

Examples of other drugs useful in the compositions and methods described herein include ceftriaxone, ceftazidime, oxaprozin, albuterol, valacyclovir, urofollitropin, famciclovir, flutamide, enalapril, fosinopril, acarbose, lorazepan, follitropin, fluoxetine, lisinopril, tramsdol, levofloxacin, zafirlukast, interferon, growth hormone, interleukin, erythropoietin, granulocyte stimulating factor, nizatidine, perindopril, erbumine, adenosine, alendronate, alprostadil, benazepril, betaxolol, bleomycin sulfate, dexfenfluramine, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, nabumetone, trovafloxacin, dolasetron, zidovudine, finasteride, tobramycin, isradipine, tolcapone, enoxaparin, fluconazole, terbinafine, pamidronate, didanosine, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Other drugs include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, rubitecan, amlodipine besylate/benazepril hydrochloride, paroxetine hydrochloride, paclitaxel, atovaquone, felodipine, podofilox, paricalcitol, betamethasone dipropionate, fentanyl, pramipexole dihydrochloride, Vitamin $D_3$ and related analogues, finasteride, quetiapine fumarate, alprostadil, candesartan, cilexetil, fluconazole, ritonavir, busulfan, carbamazepine, flumazenil, risperidone, carbidopa, levodopa, ganciclovir, saquinavir, amprenavir, carboplatin, glyburide, sertraline hydrochloride, rofecoxib carvedilol, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, lomefloxacin hydrochloride, tirofiban hydrochloride, telmisartan, diazepam, loratadine, toremifene citrate, thalidomide, dinoprostone, mefloquine hydrochloride, chloroquine, trandolapril, docetaxel, mitoxantrone hydrochloride, tretinoin, etodolac, triamcinolone acetate, estradiol, ursodiol, nelfinavir mesylate, indinavir, beclomethasone dipropionate, oxaprozin, flutamide, famotidine, prednisone, cefuroxime, lorazepam, digoxin, lovastatin, griseofulvin, naproxen, ibuprofen, isotretinoin, tamoxifen citrate, nimodipine, amiodarone, and alprazolam.

In a preferred embodiment, the acrylic polymer, includes, but is not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly (methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH insensitive or pH sensitive.

Other hydrophobic polymers useful in the present invention include ethylcellulose and polyvinyl acetate.

Channeling agents useful in the present invention include water soluble materials and or wicking agents such as cellulose ethers, polyethylene glycols, microcrystalline cellulose, lactose, sucrose, mannitol, and sorbitol The invention will be further understood from the following examples:

Example 1. Controlled Release Venlafaxine HCl Tablets

This is a two step process. In the first step, immediate release tablets are manufactured by dry granulation process followed by direct compression into tablets. In step two, three coats consisting of one or more layers of Aquacoat 30ECD (ethylcellulose polymer), Kolicoat SR 30D (polyvinyl acetate) and Eudragit NE 30D (acrylic polymer) are applied one after the other such that there is a transition from one coat to another. Note that the film forming polymers are administered separately and not as an admixture.

(1) Manufacture of Tablet

|  | Venlafaxine formulation (%) |
| --- | --- |
| Venlafaxine HCl | 20 |
| Lactose | 59 |
| Microcrystalline cellulose | 20 |
| Silicone dioxide | 0.5 |
| Magnesium stearate | 0.5 |

The materials with exception of the magnesium stearate were charged into a planetary mixer and blended for 5 minutes. The homogeneous blend was charged into a V-Blender. Magnesium stearate was added and the content blended for about 5 minutes. The blended materials were compressed into tablets in a rotary press.

(2) Coating of Tablets

The tablets were coated with an aqueous dispersion composed of ethylcellulose (Aquacoat 30ECD) plasticized with dibutyl sebacate to a 2% weight gain. This was immediately followed with a coat of polyvinyl acetate (Kolicoat SR 30D) plasticized with triethyl citrate to a weight gain of 2%. Finally a coat of Eudragit NE 30D (methacrylate copolymer) was applied to a weight of 2%. Coating was carried out in a side vented coating pan. The inlet and outlet temperature was 62 and 40 degrees centigrade respectively. Relative humidity of the coating room was 45%. The transition coated tablets were cured by drying in a tray dryer oven for 2 hours at 60° C.

Example 2. Controlled Release Metoprolol Succinate Tablets

This is a two step process. In the first step, immediate release tablets are manufactured by dry granulation process followed by direct compression into tablets. In step two, three coats consisting of one or more layers of Aquacoat 30ECD (ethylcellulose polymer), Kolicoat SR 30D (polyvinyl acetate) and Eudragit NE 30D (methacrylate copolymer) are applied one after the other such that there is a transition from one coat to another.

(1) Manufacture of Tablet

|  | Metoprolol formulation (%) |
| --- | --- |
| Metoprolol succinate | 30 |
| Lactose | 49 |
| Microcrystalline cellulose | 20 |
| Silicone dioxide | 0.5 |
| Magnesium stearate | 0.5 |

The materials with exception of the magnesium stearate were charged into a planetary mixer and blended for 5 minutes. The homogeneous blend was charged into a V-Blender. Magnesium stearate was added and the content blended for about 5 minutes. The blended materials were compressed into tablets in a rotary press.

(2) Coating of Tablets

The tablets were coated with Eudragit NE 30D to a 2% weight gain. This was immediately followed with a coat of polyvinyl acetate (Kolicoat SR 30D) plasticized with triethyl citrate to a weight gain of 2%. Finally a coat of an aqueous dispersion composed of ethylcellulose (Aquacoat 30ECD) plasticized with dibutyl sebacate was applied to a weight of 3%. Coating was carried out in a side vented coating pan. The inlet and outlet temperature was 62 and 40 degrees centigrade respectively. Relative humidity of the coating room was 45%. The transition coated tablets were cured by drying in a tray dryer oven for 2 hours at 60° C.

Example 3. Chrontherapeutic Paroxetine HCl Tablets

This is as in example 2 except for the following; paroxetine is substituted for metoprolol, hydroxypropylmethyl cellulose 5% by weight of polymer is added to the transition coat. The tablets are cured by drying in a tray dryer oven for 2 hours at 60° C. To obtain chronotherapeutic release a final coat of methacrylic acid copolymer type A (Eudragit L) is applied to 4% weight gain.

Example 4. Venlafaxine HCl Granules (1) Manufacture of Tablet

|  | Venlafaxine formulation (%) |
| --- | --- |
| Venlafaxine HCl | 20 |
| Lactose | 59 |
| Microcrystalline cellulose | 20 |
| Silicone dioxide | 1.0 |

The materials were charged into a high shear granulator and blended for 5 minutes. The homogeneous blend was granulated using Eudragit NE30D. The wet granules were screened through a 1.4 millimetre sieve using a co-mill and dried in a tray dryer oven. The dried granules were wet granulated in a planetary mixer using polyvinyl acetate (Kolicoat SR 30D) plasticized with triethyl citrate. The wet granules were dried and milled. The milled granules were filled into capsules.

We claim:
1. A controlled delivery composition for controlled release of an active ingredient consisting of:
   a tablet comprising the active ingredient;
   three coatings substantially surrounding the tablet, wherein the coatings comprise:
      a first coat consisting of polyvinyl acetate and, optionally, a plasticizer and/or a channeling agent,
      a second coat consisting of ethylcellulose and, optionally a plasticizer and/or a channeling agent, and
      a third coat consisting of methacrylate copolymer and, optionally, a plasticizer and/or a channeling agent, wherein the first coat is closest to the tablet and the third coat is the outermost coating; and
   two transition zones between the three coatings, wherein a first transition zone is located between the first and the second coating and a second transition zone is located between the second and the third coating, and
   wherein, when placed in contact with a liquid milieu, the flow of the active ingredient through the transition zones is at a cross flow relative to the flow of the active ingredient through the three coatings;
   wherein the first coat increases by about 2 wt % the weight of the controlled delivery composition compared to the weight of the tablet;
   wherein the second coat increases by about 2 wt % the weight of the controlled delivery composition compared to the weight of the tablet and the first coat;
   wherein the third coat increases by about 2 wt % the weight of the controlled delivery composition compared to the weight of the tablet, the first coat, and the second coat;
   wherein the active ingredient is an antidepressant, an antihypertensive agent, an antianginal agent, an antimanic agent, an antiarrhythmic, a thrombolytic agent, an antifibrinolytic agent, an antiplatelet agent, an anticonvulsant, an antiparkinson agent, a calcium regulation agent, an anticholinergic agent, or a hypolipidemic agent;

wherein the channeling agent is present in one or more of the coatings; and wherein the channeling agent is a cellulose ether.

2. The controlled delivery composition of claim 1, wherein the plasticizer is present in one or more of the coatings.

3. The controlled delivery composition of claim 1, wherein the controlled delivery composition provides a patient with site specific, timed, pulsed, chronotherapeutic, extended, or controlled release of the active ingredient from the tablet.

4. The controlled delivery composition of claim 1, the tablet further comprising:

at least one material selected from: a filler, a lubricant, an antioxidant, an anti-tacky agent, and a plasticizer agent.

5. The controlled delivery composition of claim 1, wherein the antidepressant is nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, venlafaxine, paroxetine, or protriptyline.

6. The controlled delivery composition of claim 1, wherein the antidepressant is venlafaxine.

7. The controlled delivery composition of claim 1, wherein the antianginal agent is metoprolol succinate.

8. A controlled delivery composition for controlled release of an active ingredient consisting of:

a tablet comprising the active ingredient;

three coatings substantially surrounding the tablet, wherein the coatings comprise:

a first coat consisting of ethylcellulose and, optionally, a plasticizer and/or a channeling agent, a second coat consisting of polyvinyl acetate and, optionally a plasticizer and/or a channeling agent, and a third coat consisting of methacrylate copolymer and, optionally, a plasticizer and/or a channeling agent, wherein the first coat is closest to the tablet and the third coat is the outermost coating; and two transition zones between the three coatings, wherein a first transition zone is located between the first and the second coating and a second transition zone is located between the second and the third coating, and wherein, when placed in contact with a liquid milieu, the flow of the active ingredient through the transition zones is at a cross flow relative to the flow of the active ingredient through the three coatings;

wherein the first coat increases by about 2 wt % the weight of the controlled delivery composition compared to the weight of the tablet;

wherein the second coat increases by about 2 wt % the weight of the controlled delivery composition compared to the weight of the tablet and the first coat;

wherein the third coat increases by about 2 wt % the weight of the controlled delivery composition compared to the weight of the tablet, the first coat, and the second coat; wherein the active ingredient is an antidepressant.

9. The controlled release composition of claim 8, wherein the antidepressant is selected from nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, venlafaxine, paroxetine, and protriptyline.

10. The controlled release composition of claim 8, wherein the antidepressant is venlafaxine.

* * * * *